(12) United States Patent
McHugh et al.

(10) Patent No.: US 7,160,551 B2
(45) Date of Patent: Jan. 9, 2007

(54) INJECTABLE SYSTEM FOR CONTROLLED DRUG DELIVERY

(75) Inventors: Anthony J. McHugh, Urbana, IL (US); Jessica R. DesNoyer, Santa Clara, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 465 days.

(21) Appl. No.: 10/191,789

(22) Filed: Jul. 9, 2002

(65) Prior Publication Data
US 2004/0009226 A1 Jan. 15, 2004

(51) Int. Cl.
*A61F 13/00* (2006.01)
*A61F 2/00* (2006.01)
*A61K 9/14* (2006.01)

(52) U.S. Cl. .............. 424/422; 424/423; 424/424; 424/425; 424/484; 424/489

(58) Field of Classification Search ............... 424/486
See application file for complete search history.

(56) References Cited

U.S. PATENT DOCUMENTS

| | | | |
|---|---|---|---|
| 4,711,782 A | 12/1987 | Okada et al. | 424/455 |
| 4,723,958 A | 2/1988 | Pope et al. | 604/890.1 |
| 4,938,763 A | 7/1990 | Dunn et al. | 604/891.1 |
| 5,213,808 A | 5/1993 | Bar-Shalom et al. | 424/473 |
| 5,302,397 A | 4/1994 | Amsden et al. | 424/473 |
| 5,330,768 A * | 7/1994 | Park et al. | 424/501 |
| 5,384,333 A | 1/1995 | Davis et al. | 514/772.3 |
| 5,516,785 A * | 5/1996 | Zoltewicz et al. | 514/334 |
| 5,626,877 A | 5/1997 | Amsden et al. | 424/489 |
| 5,702,716 A | 12/1997 | Dunn et al. | 424/422 |
| 5,702,717 A | 12/1997 | Cha et al. | 424/425 |
| 5,733,950 A | 3/1998 | Dunn et al. | 523/113 |
| 5,877,224 A | 3/1999 | Brocchini et al. | 514/772.2 |
| 5,916,598 A | 6/1999 | Rickey et al. | 424/501 |
| 5,919,484 A | 7/1999 | Shih et al. | 424/468 |
| 5,919,835 A | 7/1999 | Domb et al. | 523/113 |
| 5,962,566 A * | 10/1999 | Grandfils et al. | 524/378 |
| 6,004,573 A | 12/1999 | Rathl et al. | 424/426 |
| 6,060,518 A * | 5/2000 | Kabanov et al. | 514/781 |
| 6,117,949 A * | 9/2000 | Rathi et al. | 525/415 |
| 6,130,200 A | 10/2000 | Brodbeck et al. | 514/2 |
| 6,201,065 B1 * | 3/2001 | Pathak et al. | 525/90 |
| 6,201,072 B1 | 3/2001 | Rathl et al. | 525/415 |
| 6,287,588 B1 * | 9/2001 | Shih et al. | 424/426 |
| 6,491,903 B1 * | 12/2002 | Forster et al. | 424/78.01 |
| 2003/0045454 A1 * | 3/2003 | Okumu et al. | 514/3 |

FOREIGN PATENT DOCUMENTS

| | | |
|---|---|---|
| WO | WO 00/24374 | 5/2000 |
| WO | WO 00/24374 A1 * | 5/2000 |

OTHER PUBLICATIONS

K.J. Brodbeck, et al. Phase Inversion Dynamics of PLGA Solutions Related to Drug Delivery, Journal of Controlled Release 62 (1999), pp. 333-344.

(Continued)

*Primary Examiner*—S. Tran
(74) *Attorney, Agent, or Firm*—Evan Law Group LLC

(57) ABSTRACT

An injectable composition for delivery of a bioactive agent contains a biocompatible solvent, a hydrophobic polymer, and an amphiphilic block copolymer. The hydrophobic polymer may be a biodegradable polymer, and the block copolymer may contain a segment of poly(ethylene oxide).

37 Claims, 7 Drawing Sheets

OTHER PUBLICATIONS

J.R. DesNoyer, et al., Role of Crystallization in the Phase Inversion Dynamics and Protein Release Kinetics of Injectable Drug Delivery Systems, Journal of Controlled Release 70 (2001), pp. 285-294.

K.J. Brodbeck, et al., Sustained Release of Human Growth Hormone from PLGA Solution Depots, Pharmaceutical Research, vol. 16, No. 19 (1999), pp. 1825-1829.

Phase Inversion Dynamics of PLGA Solutions Related to Drug Delivery, Material Research Society, Mat. Res. Soc. Symp. Proc. vol. 550 (1999), pp. 41-46.

Phase Inversion Dynamics of PLGA Solutions Related to Drug Delivery, Journal of Controlled Release 58 (1999), pp. 233-245.

* cited by examiner

INJECTABLE SYSTEM FOR CONTROLLED DRUG DELIVERY

FEDERALLY SPONSORED RESEARCH DEVELOPMENT

The subject matter of this application was in part funded by the National Science Foundation (Grant no. CTS 97-31530). The government may have certain rights in this invention.

BACKGROUND

Sustained delivery of bioactive agents, especially peptide- and protein-based drug therapies, has been achieved through the use of biodegradable polymeric implants. Traditionally, this technology has involved surgical implantation of a polymeric monolith containing a suspended bioactive agent. Certain complex shapes of these monoliths have been developed to provide a constant release of the bioactive agent over a period of time. This type of release is described as zero-order, as the rate of release is constant with time. Zero-order kinetics are desirable for therapies that require the administration of a constant level of a bioactive agent.

Polymer microspheres encapsulating a bioactive agent can also be used for controlled release and are generally administered by subcutaneous injection. Although their implantation is easier than that of monoliths, the release mechanism of microspheres is rarely zero-order. An example of a microsphere system with a useful release pattern is the system having a solid polymer shell containing a blend of poly(L-lactic acid) and a bock copolymer of poly(ethylene oxide) and poly(propylene oxide) (U.S. Pat. No. 5,330,768). Encapsulation of a bioactive agent in a microsphere, however, can be difficult and expensive. Also, there is a danger of degradation of the bioactive agent due to exposure to high temperatures and denaturing solvents in the encapsulation process.

Drug release from injectable polymeric implants typically involves a mixture of biodegradable polymer and bioactive agent in a biocompatible solvent. The injectable liquid mixture solidifies upon injection into the body to form the implant. Release of the bioactive agent is provided by diffusion of the agent from the polymeric matrix, by degradation of the polymer and subsequent release of the agent into the surrounding environment, or by a combination of these two mechanisms.

Some types of polymeric implant mixtures are characterized by a premature burst release of the bioactive agent. A premature burst is an initial dose of the bioactive agent released from the mixture during or shortly after injection, that exceeds the desired dosage level and is undesirable for many therapies. Premature bursts are most often observed in implant systems that are based on solvents that readily dissolve in water and in systems which have low viscosities and are therefore relatively easy to inject through a small gauge needle.

Implant mixtures which are provided as highly viscous gels can enable delivery of the bioactive agent without a significant premature burst, but these gels typically have high viscosities and are difficult to dispense through a needle. Also, these viscous implant mixtures tend to be less compatible with the aqueous physiological environment and can be susceptible to unwanted adsorption of proteins on the implant.

BRIEF SUMMARY

In an embodiment of the invention, there is provided an injectable composition for delivery of a bioactive agent, comprising a non-aqueous biocompatible solvent, a biodegradable hydrophobic polymer, and an amphiphilic block copolymer. The biocompatible solvent is present in at least 50 percent by weight of the composition.

In another embodiment of the invention, there is provided an injectable pharmaceutical composition, comprising a bioactive agent, an amphiphilic block copolymer, a biodegradable hydrophobic polymer, and a non-aqueous biocompatible solvent. The block copolymer comprises at least one segment of poly(ethylene oxide), and the biocompatible solvent is present in at least 50 percent by weight of the composition.

In another embodiment of the invention, there is provided a method of administering a bioactive agent, comprising: inserting into an organism a pharmaceutical composition comprising a bioactive agent, an amphiphilic block copolymer, a biodegradable hydrophobic polymer, and a non-aqueous biocompatible solvent. The block copolymer comprises at least one segment of poly(ethylene oxide), and the biocompatible solvent is present in at least 50 percent by weight of the composition.

In another embodiment of the invention, there is provided a method of making an injectable composition for delivery of a bioactive agent, comprising combining ingredients including a non-aqueous biocompatible solvent, a biodegradable hydrophobic polymer, and an amphiphilic block copolymer.

In another embodiment of the invention, there is provided a kit, comprising a container and a mixture, in the container, comprising a non-aqueous biocompatible solvent, a bioactive agent, an amphiphilic block copolymer, and a biodegradable hydrophobic polymer. The biocompatible solvent is present in at least 50 percent by weight of the composition.

DETAILED DESCRIPTION

Figure 1:
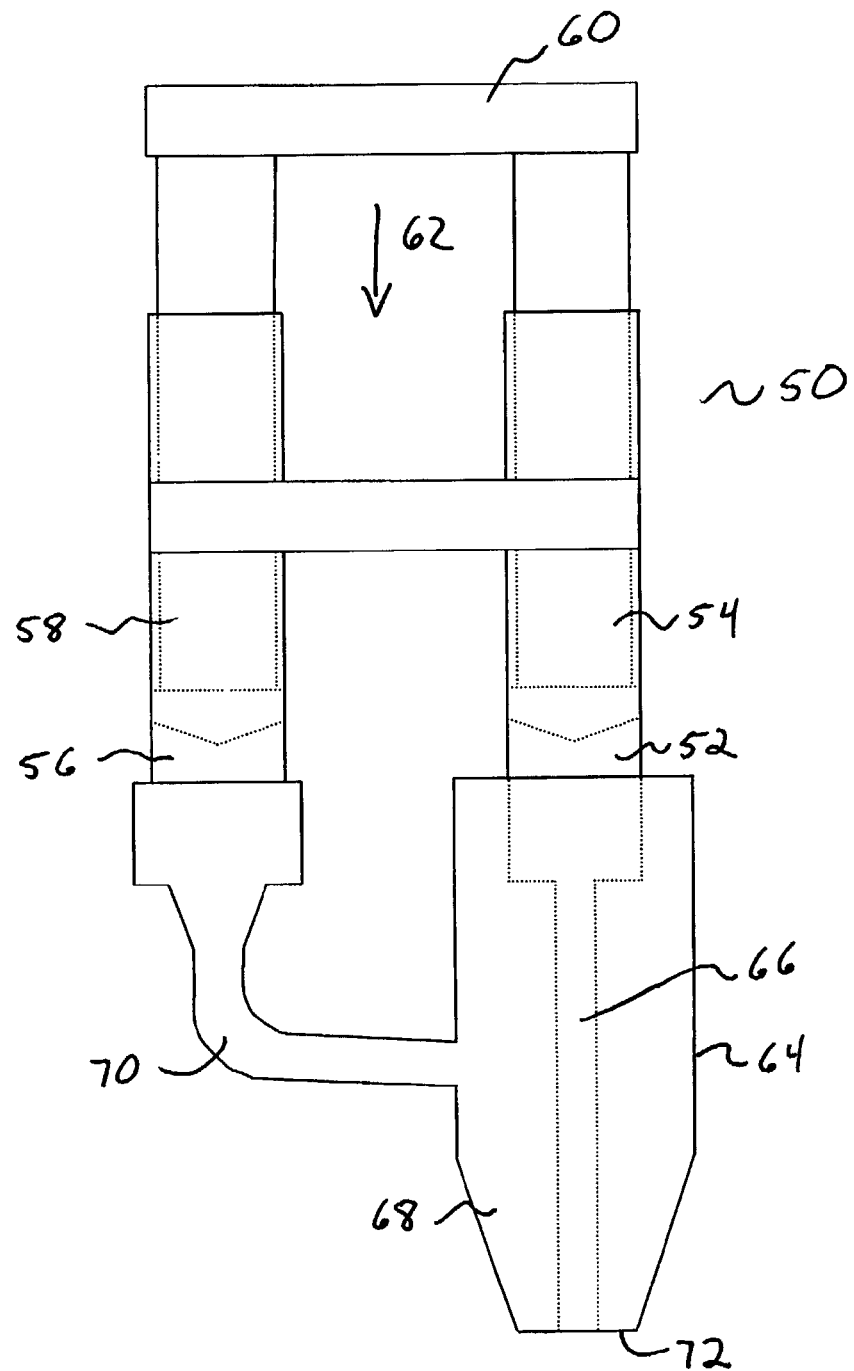
FIG. 1 is a schematic of an injection apparatus for a multi-layer depot.

The present invention includes a mixture containing a hydrophobic polymer and an amphiphilic block copolymer in a biocompatible solvent for use as an injectable implant. The implant may be used as a depot for delivery of a bioactive agent when the agent is included in the mixture. Different ratios of hydrophobic polymer to block copolymer provide for different release characteristics of the bioactive agent from the implant. These mixtures can provide for an injectable drug delivery system capable of releasing the bioactive agent in a controlled manner, with little or no initial burst release.

The term "hydrophobic polymer" means a non-crosslinked polymer having a solubility in water of less than 1 percent by weight (wt %) at 25° C. In contrast, the term "hydrophilic polymer" means a non-crosslinked polymer having a solubility in water greater than 10 wt % at 25° C. Crosslinked polymers can also be described as hydrophobic or hydrophilic, based on the hydrophobicity of non-crosslinked equivalents having molecular weights below 500,000 daltons. For example, a crosslinked poly(ethylene oxide) is considered hydrophilic since a non-crosslinked poly(ethylene oxide) has an aqueous solubility greater than 50 wt % at 25° C.

Hydrophobic polymers for use with the present invention are preferably biodegradable polymers. Biodegradable polymers decompose when placed inside an organism and thus eliminate the need to remove the implant after the bioactive agent has been released, since the polymer will gradually break down and may be metabolized or excreted from the body. The decomposition of a biodegradable polymer can be observed as a decline in the molecular weight of the polymer over time. Polymer molecular weights can be determined by a variety of methods including size exclusion chromatography (SEC), and are generally expressed as weight averages or number averages. A polymer is determined to be biodegradable or non-biodegradable by the following test. A solution of the polymer in N-methyl pyrrolidone (NMP) is added to phosphate buffered saline (PBS) of pH 7.4 and maintained at a temperature of 37° C. The weight average molecular weight is measured by SEC at the start of the test and then measured by SEC periodically over time. A polymer is biodegradable if its weight average molecular weight, as measured by SEC, is reduced by at least 25% relative to the starting weight average molecular weight over a period of 6 months.

Hydrophobic polymers which are useful for the present invention include polyesters, such as poly(caprolactone), poly(glycolic acid), poly(lactic acid), poly(hydroxybutryate); copolymers of caprolactone, glycolic acid, lactic acid, and hydroxybutryate; polyanhydrides, such as poly(adipic anhydride); poly(para-dioxanone); poly(malic acid); polyamines; polyurethanes; polyesteramides; polyorthoesters; polyacetals; polyketals; polycarbonates; polyorthocarbonates; polyphosphazenes; poly(amino acids); chitin; chitosan; and copolymers and mixtures thereof.

Amphiphilic block copolymers are non-crosslinked polymers containing at least one segment of a hydrophobic polymer connected to at least one segment of a hydrophilic polymer. A segment of a polymer preferably contains at least five repeating units of that polymer linked together. The block copolymers may be di-block copolymers, tri-block copolymers, or multi-block copolymers, and the block copolymers may be configured as linear chains or as grafted chains, including comb copolymers and star copolyrners. Preferably, each segment is made of polymer which is non-toxic when present in an organism apart from any other polymer segment(s).

Examples of hydrophobic polymers, segments of which may be included in an amphiphilic block copolymer, include the hydrophobic polymers listed above as well as non-biodegradable hydrophobic polymers such as poly(propylene oxide), poly(butylene oxide), polyolefins, polystyrene, poly(dimethyl siloxane), and polyimides.

Examples of hydrophilic polymers, segments of which may be included in an amphiphilic block copolymer, include poly(ethylene oxide), poly(acrylamide), poly(vinyl alcohol), poly(vinylpyrrolidone), hydroxylated cellulose, carboxylated polymers such as carboxycellulose, and sulfonated polymers such as sulfonated polystyrene. General classes of polymers such as polyesters, polycarbonates, polyurethanes, and polyphosphazenes can be either hydrophilic or hydrophobic, depending on the composition of pendant groups and segments in the backbone.

Preferred amphiphilic block copolymers include block copolymers containing poly(ethylene oxide) segments and/or poly(propylene oxide) segments as the hydrophilic and hydrophobic blocks, respectively. Examples of these block copolymers include the poly(ethylene oxide)-co-poly(propylene oxide)-co-poly(ethylene oxide) and poly(propylene oxide)-co-poly(ethylene oxide)-co-poly(propylene oxide) block copolymers available from BASF under the name PLURONIC.

Preferably, the hydrophobic polymer has a weight average molecular weight from about 1,000 daltons to about 500,000 daltons. More preferably, the hydrophobic polymer has a weight average molecular weight from about 10,000 daltons to about 250,000 daltons; and even more preferably, the hydrophobic polymer has a weight average molecular weight from about 25,000 daltons to about 100,000 daltons. Preferably, the amphiphilic block copolymer has a weight average molecular weight from about 500 daltons to about 250,000 daltons. The weight average molecular weight of the amphiphilic block copolymer is more preferably from about 1,000 daltons to about 100,000 daltons; even more preferably from about 1,500 daltons to about 50,000 daltons; and even more preferably from about 2,000 daltons to about 15,000 daltons. Preferably, the weight ratio of hydrophobic polymer to amphiphilic block copolymer is about 10:1 or less. The weight ratio of hydrophobic polymer to amphiphilic block copolymer is more preferably about 5:1 or less; even more preferably about 4:1 or less; even more preferably about 3:1 or less; and even more preferably about 2:1 or less. These preferred ranges for the weight ratio of hydrophobic polymer to amphiphilic block copolymer include intermediate ratios such as 3.5:1, 2.3:1, and 1.5:1. Preferably, the weight ratio of hydrophobic polymer to amphiphilic block copolymer is from about 10:1 to about 1:1.

It is typically desirable to combine the hydrophobic polymer, amphiphilic block copolymer and bioactive agent in an appropriate non-aqueous solvent. The non-aqueous solvent preferably is biocompatible and miscible with water. The term biocompatible means a substance which is not toxic, harmful, or immunogenic when present in an organism in an amount appropriate for normal use. The term solvent, unless specifically indicated otherwise, means a single solvent or a mixture of solvents. The solvent or solvent mixture is capable of dissolving or dispersing the polymer to form a mixture that can maintain particles of a bioactive agent dissolved or dispersed and isolated from the environment of use prior to release.

Preferred biocompatible solvents are miscible in water, that is having a solubility in water of greater than 50 wt %. Water miscibility may be determined experimentally as follows: Water (1–5 g) is placed in a tared clear container at a controlled temperature, about 20° C., and weighed, and a candidate solvent is added dropwise. The solution is swirled to observe phase separation. When the saturation point appears to be reached, as determined by observation of phase separation, the solution is allowed to stand overnight and is checked again the following day. If the solution is still saturated, as determined by observation of phase separation, then the percent by weight of solvent added is determined. Otherwise more solvent is added and the process repeated. Solubility or miscibility is determined by dividing the total weight of solvent added by the final weight of the solvent/water mixture. When solvent mixtures are used, they are pre-mixed prior to addition to the water.

Preferred biocompatible solvents include, but are not limited to, diacetin, tributyrin, triethyl citrate, tributyl citrate, acetyl triethyl citrate, acetyl tributyl citrate, triethylglycerides, triethyl phosphate, diethyl phthalate, diethyl tartrate, polybutene, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, 1-dodecylazacycloheptan-2-one, and mixtures thereof.

An emulsifying agent or a component solvent may optionally be added to the composition to reduce the viscosity. Emulsifying agents include, for example, solvents that are not fully miscible with the polymer solvent or solvent mixture. Examples of emulsifying agents include alcohols, polyols, esters, carboxylic acids, ketones, aldehydes, naturally occurring gums, for example gum acacia or gum tragacanth; naturally occurring phosphatides, for example soy bean and lecithin; esters or partial esters derived from fatty acids and hexitol anhydrides, for example sorbitan monooleate; or condensation products of the partial esters with ethylene oxide, for example polyoxyethylene sorbitan monooleate. Also, since the viscosity may typically be lowered as the temperature of the composition increases, it may be advantageous in certain applications to reduce the viscosity of the mixture by heating to provide a more readily injectable composition.

Suspensions may contain the bioactive materials in admixture with excipients suitable for the manufacture of suspensions. Such excipients include suspending agents, for example sodium carboxymethylcellulose, methylcellulose, hydroxypropylmethylcellulose, sodium alginate, polyvinylpyrrolidone, gum tragacanth and gum acacia. Excipients may include dispersing or wetting agents, which may be a naturally-occurring phosphatide, for example lecithin; or condensation products of an alkylene oxide with fatty acids, for example polyoxyethylene stearate; or condensation products of ethylene oxide with long chain aliphatic alcohols, for example heptadecaethyleneoxycetanol; or condensation products of ethylene oxide with partial esters derived from fatty acids and a hexitol such as polyoxyethylene sorbitol monooleate; or condensation products of ethylene oxide with partial esters derived from fatty acids and hexitol anhydrides, for example polyethylene sorbitan monooleate. The aqueous suspensions may also contain one or more preservatives, for example ethyl- or n-propyl-p-hydroxybenzoate. Suspensions may be formulated by suspending the bioactive ingredient in a vegetable oil, for example arachis oil, olive oil, sesame oil or coconut oil; or in a mineral oil such as liquid paraffin. The suspensions may contain a thickening agent, for example beeswax, hard paraffin or cetyl alcohol. These compositions may be preserved by the addition of an anti-oxidant such as ascorbic acid.

Dispersible powders and granules suitable for preparation of a suspension by the addition of liquid provide a bioactive ingredient in admixture with a dispersing or wetting agent, suspending agent and one or more preservatives. Suitable dispersing or wetting agents and suspending agents are exemplified by those already mentioned above. Additional excipients may also be present.

The bioactive agent can be any physiologically or pharmacologically active substance or substances optionally in combination with pharmaceutically acceptable carriers and additional ingredients such as antioxidants, stabilizing agents, permeation enhancers, etc. that do not substantially adversely affect the advantageous results that can be attained. The bioactive agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, antiinflammatory corticosteroids, ocular drugs, antiinflammatory agents, antitussives and expectorants, sedatives, muscle relaxants, antiepileptics, antiulcer agents, antidepressants, antiallergic drugs, cardiotonics, antiarrhythmic agents, vasodilators, antihypertensive diuretics, antidiabetics, anticoagulants, haemostatics, antituberculotics, hormone drugs, antinarcotics, and synthetic analogs of these species.

Examples of drugs which may be delivered by the composition of the present invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat captopril, ramipril, famotidine, nizatidine, sucralfate, etintidine, tetratolol, minoxidil, chlordiazepoxide, diazepam, amitriptyline, and imipramine.

Examples of antibiotics include gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam.

Examples of antipyretic, analgesic and antiinflammatory drugs include sodium salicylate, sulpyrine, sodium flufenamate, sodium diclofenac, sodium indomethacin, morphine hydrochloride, pethidine hydrochloride, levorphanol tartrate and oxymorphone. Examples of antitussives and expectorants include ephedrine hydrochloride, methylephedrine hydrochloride, noscapine hydrochloride, codeine phosphate, dihydrocodeine phosphate, alloclamide hydrochloride, chlophedianol hydrochloride, picoperidamine hydrochloride, cloperastine, protokylol hydrochloride, isoproterenol hydrochloride, salbutamol sulfate and terbutaline sulfate.

Examples of sedatives include chlorpromazine hydrochloride, prochlorperazine, trifluoperazine, atropine sulfate and scopolamine methylbromide. Examples of muscle relaxants include pridinol methanesulfonate, tubocurarine chloride and pancuronium bromide. Examples of antiepileptics include sodium phenytoin, ethosuximide, sodium acetazolamide and chlordiazepoxide hydrochloride.

Examples of antiulcer drugs include metoclopramide and L-histidine monohydrochloride. Examples of antidepressants include imipramine, clomipramine, noxiptiline and phenelzine sulfate. Examples of antiallergic drugs include diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride.

Examples of cardiotonics include trans-π-oxocamphor, theophyllol, aminophylline and etilefrine hydrochloride. Examples of antiarrythmic agents include propranolol hydrochloride, alprenool hydrochloride, bufetolol hydrochloride and oxyprenolol hydrochloride. Examples of vasodilators include oxyfedrine hydrochloride, diltiazem hydrochloride, tolazoline hydrochloride, hexobendine and bamethan sulfate. Examples of antihypertensive diuretics include hexamethonium bromide, pentolinium, mecamylamine hydrochloride, ecarazine hydrochloride and clonidine hydrochloride.

Examples of antidiabetics include sodium glymidine, glypizide, phenformin hydrochloride, buformin hydrochloride and metformin. Examples of anticoagulants include sodium heparin and sodium citrate. Examples of haemostatic agents include thromboplastin, thrombin, menadione sodium bisulfite, acetomenaphthone, ε-amino-caproic acid, tranexamic acid, carbazochrome sodium sulfonate and adrenochrome monoaminoguanidine methanesulfonate. Examples of antituberculotics include isoniazid, ethambutol and sodium p-aminosalicylate.

Examples of hormone drugs include prednisolone succinate, prednisolone sodium phosphate, dexamethasone sodium sulfate, betamethasone sodium phosphate, hexestrol phosphate, hexestrol acetate and methimazole. Examples of antinarcotic agents include levallorphan tartrate, nalorphine hydrochloride and naloxone hydrochloride.

Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, bovine growth hormone and porcine growth hormone, fertility inhibitors such as the prostaglandins, fertility promoters, growth factors such as insulin-like growth factor, coagulation factors, human pancreas hormone releasing factor, analogs and derivatives of these compounds, and pharmaceutically acceptable salts of these compounds, or their analogs or derivatives.

The present invention also finds application with chemotherapeutic agents for the local application of such agents to avoid or minimize systemic side effects. Mixtures of the present invention containing chemotherapeutic agents may be injected directly into the tumor tissue for sustained delivery of the chemotherapeutic agent over time. In some cases, particularly after resection of the tumor, the mixture may be implanted directly into the resulting cavity or may be applied to the remaining tissue as a coating. In cases in which the mixture is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, BCNU, vincristine, camptothecin, etopside, bleomycin hydrochloride, methotrexate, actinomycin D, mitomycin C, vinblastine sulfate, vincristine sulfate, daunorubicin hydrochloride, adriamycin, neocarcinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U and poly ICLC, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as for example cisplatin and carboplatin and the water soluble derivatives of paclitaxel. To the extent not mentioned above, the bioactive agents described in aforementioned U.S. Pat. No. 5,242,910 can also be used.

Compositions for delivery of a bioactive agent can be prepared by a variety of methods. The hydrophobic polymer and amphiphilic block copolymer can be combined and then mixed with the biocompatible solvent, or the hydrophobic polymer and amphiphilic block copolymer can be mixed with the solvent separately. A mixture of the hydrophobic polymer with a solvent can be combined with a mixture of the amphiphilic block copolymer with a solvent, and these solvents may be the same or they may be different. The bioactive agent can be combined with either or both of the hydrophobic polymer and the amphiphilic block copolymer before mixing with the solvent, or the bioactive agent can be combined with the mixture of hydrophobic polymer, amphiphilic copolymer, and solvent. The hydrophobic polymer and/or the amphiphilic block copolymer can be formed directly in the solvent, for example by polymerization or by linking prepolymers or polymer segments. In one example, mixtures of the hydrophobic polymer and amphiphilic copolymer with the solvent can be provided in discrete portions. These portions can then be mixed with a unit dosage of bioactive agent for immediate use or for storage or shipment.

The hydrophobic polymer, amphiphilic block copolymer, solvent, and any emulsifying agent or excipient used in the mixture are preferably pharmaceutically acceptable carriers. The pharmaceutical compositions for the administration of the bioactive agents may conveniently be presented in dosage unit form and may be prepared by any of the methods well known in the art of pharmacy. All methods include the step of bringing the bioactive agent into association with the carrier that constitutes one or more accessory ingredients. Preferably, the pharmaceutical compositions are prepared by uniformly and intimately bringing the bioactive agent into association with a liquid carrier. In the pharmaceutical composition the bioactive agent is included in an amount sufficient to produce the desired effect upon the process or condition of diseases.

The bioactive agent can be incorporated into the injectable mixture formed from the hydrophobic polymer, the amphiphilic block copolymer and the biocompatible solvent in the form of particles typically having an average particle size of from about 0.1 to about 100 microns, or from about 1 to about 25 microns, or further from 2 to 10 microns. For example, particles having an average particle size of about 5 microns may be produced by spray drying or freeze drying. Conventional lyophilization processes can also be utilized to form particles of bioactive agents of varying sizes using appropriate freezing and drying cycles.

To form a suspension or dispersion of particles of the bioactive agent in the mixture formed from the hydrophobic polymer, the amphiphilic block copolymer and the biocompatible solvent, any conventional low shear device can be used, such as a ROSS double planetary mixer (ROSS, Hauppauge, N.Y.) at ambient conditions. In this manner, efficient distribution of the bioactive agent can be achieved substantially without degrading the bioactive agent. The amount of bioactive agent in the mixture is preferably equal to a unit dosage. A unit dosage is the amount of bioactive agent necessary to produce the desired beneficial effect in the organism to which it is administered. The absolute amount of a unit dosage can depend on many factors including, for example, the type of agent, the efficacy of the agent, the health of the organism, and the size of the organism.

Mixtures as described may be administered in a variety of ways. Preferred methods of administration involve injection. Injection may be subcutaneous, parenteral, or other types of injection known to those skilled in the art. A consideration for administration by injection is the viscosity of the mixture, which should be low enough to allow for transmission of the mixture through a needle. It is preferred that the viscosity is such that the mixture can be made to flow easily through an 18–20 gauge needle or smaller needle. More preferably, the mixture has a viscosity from 0.1 to 10 pascal-seconds (Pa-s) at 25° C. Even more preferably, the mixture has a viscosity from 0.5 to 7 Pa-s at 25° C.

For mixtures to be administered by injection, the hydrophobic polymer and amphiphilic block copolymer should be non-crosslinked before they are inserted into a subject. Chemically crosslinked polymers are sometimes referred to as network polymers, since they do not dissolve but rather form an insoluble three dimensional network. Chemically crosslinked polymers may swell in a solvent, but the swollen gel will be difficult or impossible to transmit through a needle. It may be desirable for the hydrophobic polymer and/or the amphiphilic block copolymer to form a crosslinked network after injection.

It is preferred that the hydrophobic polymer and the amphiphilic block copolymer form a miscible solution when combined with the biocompatible solvent. Preferably, injectable mixtures contain at least about 50 wt % of the biocompatible solvent. More preferably, injectable mixtures contain at least about 60 wt % of the biocompatible solvent. The balance of the weight of the mixture is formed of the hydrophobic polymer, the amphiphilic block copolymer, the bioactive agent, and any excipients or emulsifiers. It is preferred that the entire mixture is sterile.

For an implant administered by injection, the fluid mixture transforms into a depot upon contact with the native fluid in the body. This depot is characterized by its phase separation from the physiological fluid and its decreased fluidity relative to the original mixture. The depot may be a semi-fluid gel, it may be a solid, or it may have an intermediate rigidity. It is this depot that serves as the polymeric implant for controlled release of the bioactive agent.

Since the implant systems of the present invention may also be formed as viscous gels, the means of administration of the implants is not limited to injection, although that mode of delivery may often be preferred. Where the implant will be administered as a leave-behind product, it may be formed to fit into a body cavity existing after completion of surgery or it may be applied as a flowable gel by brushing or palleting the gel onto residual tissue or bone. Such applications may permit loading of bioactive agent in the mixture at concentrations above those typically present in injectable compositions. It is also possible to form the depot outside the body and then to implant the depot surgically. In this case, the mixture can be formed, and then the solvent removed, for example by evaporation. Alternatively, the polymers can be extruded and layered.

Multi-layer, or composite, depots can also be formed. Composite depots can provide complex release profiles, including multiple stages of controlled burst release and controlled gradual release. Composite depots can be formed by supplying the injection needle with a mixture having a composition which changes during the injection process. For example, the initial composition may contain only hydrophobic polymer, the final composition may contain only amphiphilic block copolymer, while the intermediate composition contains a blend of these polymers.

The composite formulation may be administered by injection of a composition that is itself layered. FIG. 1 illustrates a syringe 50 that is useful for preparing such layered injections. This syringe has two reservoirs 52 and 56 equipped with plungers 54 and 58 connected by a common handle 60. The reservoirs can be supplied with two different mixtures, for example a mixture containing only hydrophobic polymer in one reservoir and a mixture containing both hydrophobic polymer and amphiphilic block copolymer in the other. A force on the handle in the direction of arrow 62 forces both mixtures into the dispensing area 64, which contains two chambers. The mixture in reservoir 52 is displaced into inner chamber 66, and the mixture in reservoir 56 is displaced into outer chamber 68 through tube 70. Both chambers are connected to opening 72 through which the layered mixture is dispensed. The opening 72 may be connected to a needle having a proper length and gauge to permit the layered mixture to be injected into an organism.

Alternatively, the syringe 50 may be used to form a composite depot ex vivo, and the depot may be surgically inserted into an organism.

Figure 2:
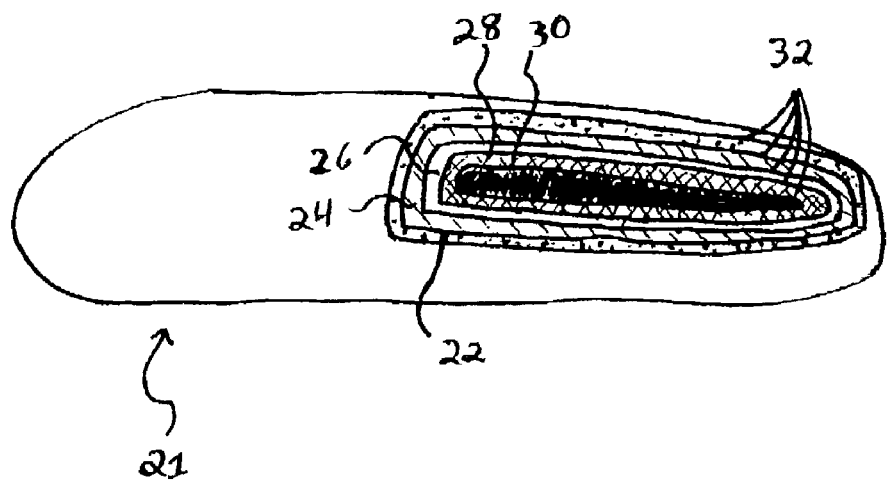
FIG. 2 is a cut-away view of a multi-layer depot.

Composite depots can be formed by combining layers of a depot formulation ex vivo. For example, a process of depositing mixtures separately into a receptor buffer can be used to make a laminate, a layered disk, a series of concentric spheres, or any formed object. The formed depot may then be inserted surgically into the organism. An example of a composite depot is pictured in FIG. 2. Depot 21 may contain gel layers 22, 24, 26, 28, and 30. These layers may be separated by a barrier layer 32. This barrier layer may be a semi-permeable membrane such that water and bioactive agent can pass through the membrane, but the gel layers are prevented from mixing. This membrane is preferably biodegradable and insoluble in the solvent in the mixture. For example, the exterior of a gel layer can be coated with a solution of poly(L-lactide) in dichloromethane. Evaporation of the volatile solvent will provide a layer of poly(L-lactide) around the gel layer. The semicrystalline poly(L-lactide) layer is biodegradable, but will dissolve very slowly or not at all in the biocompatible solvent present in the gel.

The gel layers in the composite depot 21 can have a variety of compositions. They may be alternated such that every other layer contains amphiphilic block copolymer, and the remaining layers contain only hydrophobic polymer. They may all contain amphiphilic block copolymer, and the type and relative amount of amphiphilic block copolymer may be different or may independently be the same for at least two layers. A composite depot may contain at least one layer in which the solvent is immiscible with water, providing for slower water uptake for that particular layer. A composite depot may contain at least one layer containing a biodegradable crystallizable polymer, optionally mixed with a biodegradable amorphous polymer, as described in copending application Ser. No. 09/733,640, filed Dec. 8, 2000 with inventors A. J. McHugh and J. DesNoyer, and commonly assigned to the Trustees of the University of Illinois, which is incorporated herein by reference. The release profile for each layer will be affected by its composition. Thus, a complex release profile for the entire depot 21 can be designed by selection and ordering of the gel layers. Complex release profiles may be particularly effective for vaccinations, for example Hepatitis-B vaccine.

Figure 3:
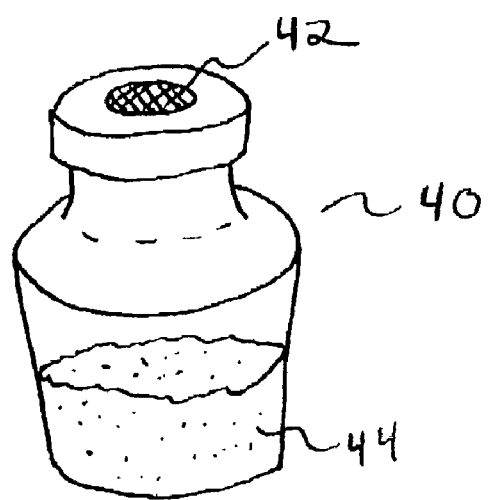
FIG. 3 is a view of a kit.

An injectable mixture may be conveniently packaged in a sterile container, such as the vial 40 illustrated in FIG. 3. This container may be part of a kit which may optionally contain a sterile syringe and needle. The vial 40 may be sealed with a septum 42. This septum seals the mixture 44 and may be pierced by a needle and syringe to permit withdrawal of the mixture. The vial may contain all the ingredients necessary for the controlled release of the bioactive agent. It is preferred that end user of the mixture not be required to add further ingredients or to measure the dosage prior to administration.

The pattern of release over time of the bioactive agent after administration of the mixture may be affected by the type and relative amount of the components of the mixture. The presence of an amphiphilic block copolymer together with a hydrophobic polymer can provide for gradual release of the bioactive agent without a significant premature burst release. Preferably, less than about 20% of the bioactive agent is released within 24 hours of administration of the mixture. More preferably, less than about 10% of the bioactive agent is released within 24 hours of administration. Even more preferably, less than about 5% of the bioactive agent is released within 24 hours of administration. In addition to little or no premature burst release, it is also preferred that the bioactive agent is released gradually over time. Preferably, less than about 50% of the bioactive agent is released within 200 hours of administration of the mixture.

When a mixture of the present invention is placed into an aqueous environment, such as the physiological environment of an organism or an aqueous medium of a controlled laboratory setting, the non-aqueous biodegradable solvent and the water of the aqueous surroundings will begin to mix. The mixing of the solvent and the water can be accelerated if the solvent is miscible with water. An increase in the concentration of water in the mixture can provide for phase separation of the mixture into discrete regions, with some regions containing a higher ratio of hydrophobic polymer to amphiphilic block copolymer and other regions containing a lower ratio. In conventional systems, phase separation tends to form channels or pores, providing for a premature burst release of the bioactive agent since the agent is more easily transported away from the depot. Without wishing to be bound by any theory of operation, it is believed that at least the hydrophilic segments of the amphiphilic block copolymer accumulate in the pores or channels formed during the phase separation. The presence of these segments serves to inhibit the displacement of the bioactive agent, reducing or eliminating the premature burst and instead allowing for a slow, gradual release of the agent.

A system containing a hydrophobic polymer, an amphiphilic block copolymer and a biocompatible solvent may be optimized to provide for high, low, or intermediate premature burst, as well as for a desired rate of release. In addition, various combinations of more than one hydrophobic polymer, more than one amphiphilic block copolymer and/or more than one biocompatible solvent can be used to provide for a specific release profile. For example, in the combination of poly(D,L-lactide), PLURONIC L101 and N-methyl pyrrolidone (NMP), the premature burst release decreases with increasing loading of the amphiphilic block copolymer to a ratio of hydrophobic polymer to amphiphilic block copolymer of 1.5 or lower.

EXAMPLES

Poly(D,L-lactide) (PDLA) was obtained from BOEHRINGER INGELHEIM (Ridgefield, CT) as RESOMER 208, with an intrinsic viscosity (i.v.) of 1.8 deciliters per gram (dL/g). Poly(lactide-co-glycolide), NMP (1-methyl-2-pyrrolidinone), and ethyl benzoate were obtained from ALDRICH (Milwaukee, Wis.).

PLURONIC triblock copolymers having the structure poly(ethylene oxide)-poly(propylene oxide)-poly(ethylene oxide) were obtained from BASF Corporation (Mount Olive, N.J.). PLURONIC L101 has an average molecular weight of 3800 daltons and contains poly(ethylene oxide) repeat units at a 10 wt % level. PLURONIC L121 has an average molecular weight of 4400 daltons and contains poly(ethylene oxide) repeat units at a 10 wt % level. Thus, the structures of L101 and L121 are proportional, with L121 having larger segments of both poly(propylene oxide) and poly(ethylene oxide) than L101, but with the same ratio of block lengths.

Chicken egg white lysozyme (Muramidase, or mucopeptide N-acetylmuramoyl-hydrolase, Enzyme Commission Number 3.2.1.17) was obtained from SIGMA (Milwaukee, Wis.). The activity of the lysozyme was approximately 48,000 units per milligram protein, and the lysozyme was triple crystallized, dialyzed and lyophilized to a 95% protein level, with the balance primarily buffer salts (sodium acetate and sodium chloride).

Example 1

A polymer mixture was prepared by mixing PDLA with N-methyl pyrrolidone (NMP) at a 20 wt % loading of the polymer. Mixing was carried out in a 10 cm$^3$ glass vial at room temperature for several hours to ensure complete dissolving of the polymer and removal of all air bubbles. Due to the hygroscopic nature of the solvent, solutions were used within 24 hours of preparation. Composition of the mixture is given in Table 1.

Examples 2–4

Polymer mixtures were prepared as in Example 1, except using mixtures of PDLA and PLURONIC L101 at weight ratios of 4:1, 2.3:1 and 1.5:1. The total polymer loading in each mixture was maintained at 20 wt %. The compositions of the mixtures are given in Table 1.

Example 5

A polymer mixture was prepared as in Examples 2–4, except using a mixture of PDLA and PLURONIC L121 at a weight ratio of 2.3:1. The total polymer loading in the mixture was maintained at 20 wt %. The composition of the mixture is given in Table 1.

TABLE 1

| Example | Composition in weight percent | | | |
|---|---|---|---|---|
| | PDLA | L101 | L121 | NMP |
| 1 | 20 | — | — | 80 |
| 2 | 16 | 4 | — | 80 |
| 3 | 14 | 6 | — | 80 |
| 4 | 12 | 8 | — | 80 |
| 5 | 14 | — | 6 | 80 |

Example 6

Water Uptake

In-situ imaging of the phase inversion dynamics was done using the dark ground imaging (DGI) apparatus and techniques as described in P. D. Graham et al. *J. Control. Rel.* 58 (1999) 233–245. The phase inversion kinetics were quantified in terms of the propagation rate of the leading edge of the liquid de-mixing zone (L-I Front) that developed on exposing the polymer mixture to a quench medium of phosphate buffered saline (PBS, pH 7.4). Each mixture precipitated as a semi-solid mass and hardened to a solid, 'rubber-like' gel that could be extracted readily from the diffusion cell.

Figure 4:
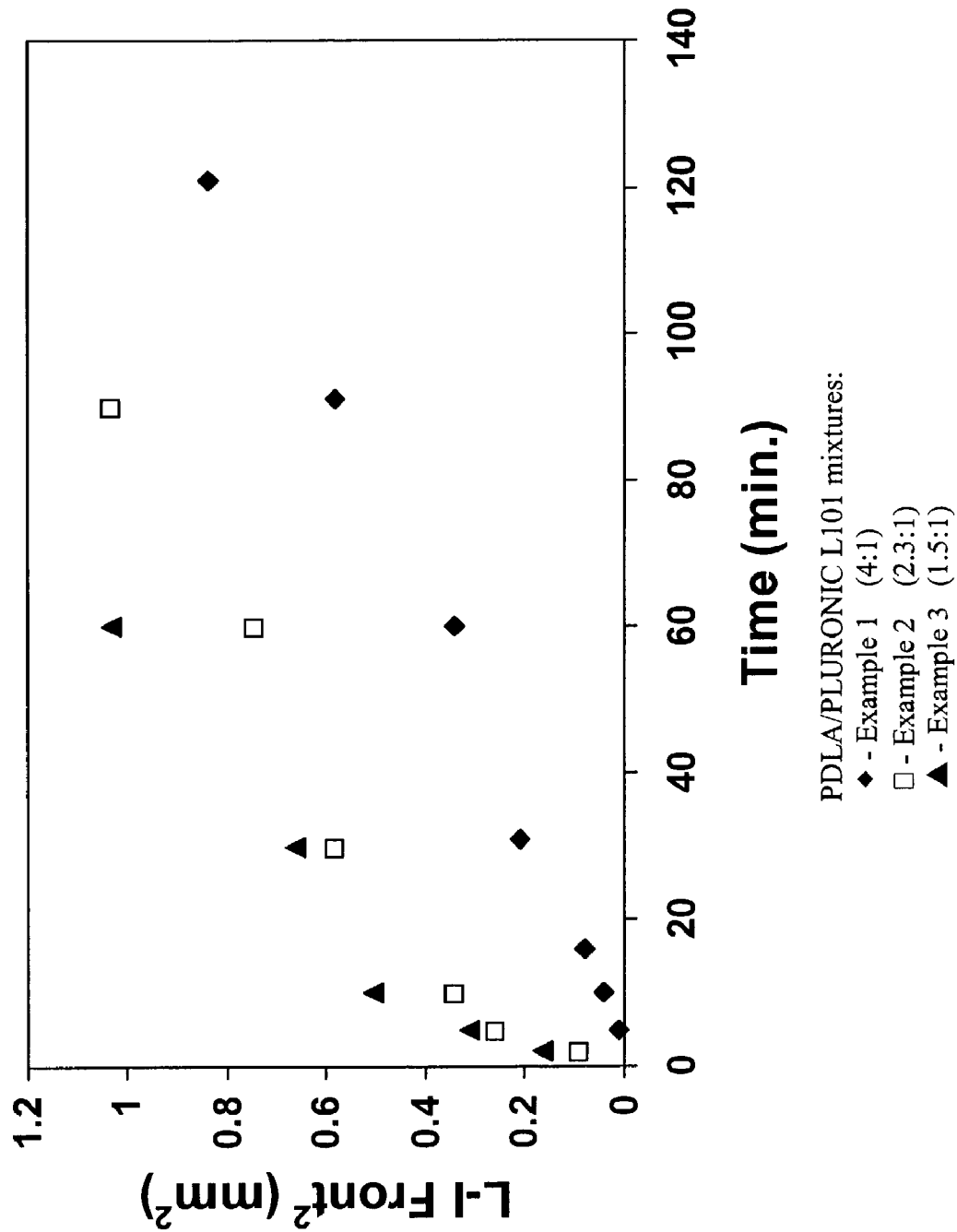
FIGS. 4–5 are graphs of results from liquid-liquid phase separation studies.
Figure 5:
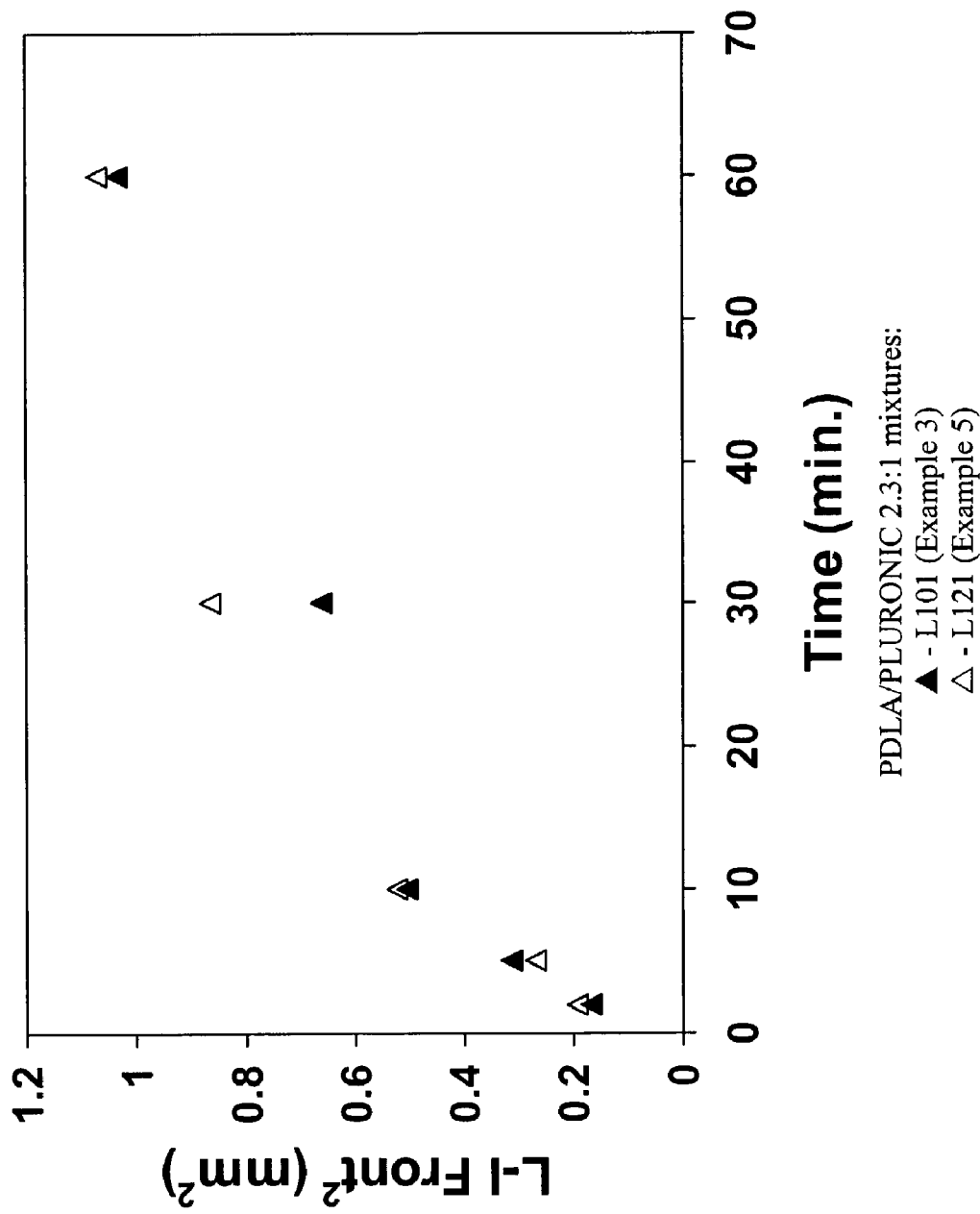

The kinetics of the liquid demixing front motion is shown in FIG. 4 for PDLA/L101 mixtures with various L101 concentrations. The L-I Front (mm$^2$) is plotted as a function of time. Mixtures with increasing amounts of the amphiphilic block copolymer phase separated more rapidly. The graph of FIG. 5 shows that an increase in the ethylene oxide block length from the L101 copolymer to the L121 copolymer had a negligible effect on the liquid de-mixing rate of the blend solution. Although PLURONIC L101 and PLURONIC L121 have a relatively low content of the hydrophilic ethylene oxide blocks (10 wt %), the amphiphilic block copolymers still increase the water uptake and liquid de-mixing rates in PDLA blend depots.

Example 7

A polymer mixture was prepared by mixing poly(lactide-co-glycolide) (PLGA) in ethyl benzoate (ALDRICH) at a 50 wt % loading.

Example 8

Viscosity of Formulations

Viscosity measurements were carried out on the PDLA/PLURONIC mixtures of Examples 2–4, as well as on the PLGA/ethyl benzoate comparative mixture of Example 7. The viscosity measurements were preformed under simple shear using an AR 1000-N (TA INSTRUMENTS, New Castle, DE) constant stress rheometer with a cone and plate geometry. Data were taken with a 4 cm, 2° and a 2 cm, 2° cone. A solvent trap was used to prevent evaporation, and experiments were performed at 25° C. and 37° C. using a Peltier plate (0–100° C.) to control temperature to a precision of 0.1° C.

Figure 6:
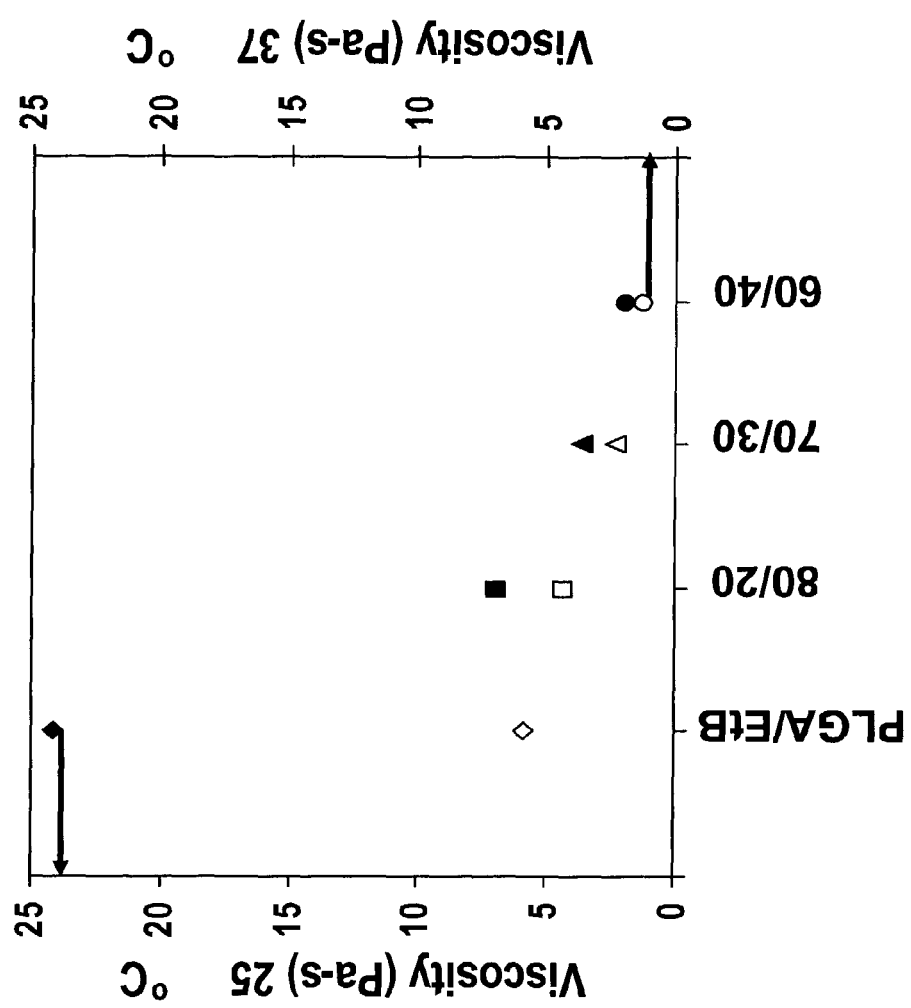
FIG. 6 is a graph of results from viscosity studies.

FIG. 6 shows a comparison of the Newtonian viscosities at 25° C. and 37° C. for the amphiphilic block copolymer containing systems of Examples 2–4, as well as the 50 wt. % PLGA/ethyl benzoate formulation. The PLGA/ethyl benzoate system has been shown to exhibit desirable release kinetics, and the viscosity of this system at 37° C. is sufficiently low to allow injection through a 20 gauge needle at 2 cubic centimeters per minute (cc/min). However this viscous, hydrophobic system has a viscosity at room temperature (25° C.) which is five times the viscosity at 37° C. The formulations containing PLURONIC L101 have viscosities at room temperature which are comparable to or less than the viscosity of the PLGA/ethyl benzoate system at elevated temperature. Thus, the PLURONIC containing formulations can have improved injectability over the PLGA/ethyl benzoate system.

Example 9

A polymer mixture was prepared by mixing PDLA with NMP at a 20 wt % loading of the polymer, as in Example 1. Lysozyme particles were then added to the polymer solution at a level of 10% by weight of the total formulation. Composition of the mixture is given in Table 2.

Examples 10–12

Polymer mixtures were prepared in Example 9, except using mixtures of PDLA and PLURONIC L101 at weight ratios of 4:1, 2.3:1, and 1.5:1. The total polymer loading in each mixture was maintained at 20 wt %, and the total lysozyme loading was 10 wt %. The compositions of the mixtures are given in Table 2.

Example 13

A polymer mixture was prepared as in Examples 10–12, except using a mixture of PDLA and PLURONIC L121 at a weight ratio of 2.3:1. The total polymer loading in the mixture was maintained at 20 wt %, and the total lysozyme loading was 10 wt %. The composition of the mixture is given in Table 2.

TABLE 2

| | Composition in weight percent | | | | |
|---|---|---|---|---|---|
| Example | PDLA | L101 | L121 | NMP | Lysozyme |
| 9 | 18 | — | — | 72 | 10 |
| 10 | 14.4 | 3.6 | — | 72 | 10 |
| 11 | 12.6 | 5.4 | — | 72 | 10 |
| 12 | 10.8 | 7.2 | — | 72 | 10 |
| 13 | 12.6 | — | 5.4 | 72 | 10 |

Example 14

Protein Release

Chicken egg white lysozyme was used as the model bioactive agent released from the depot. Protein release experiments were conducted in a HANSON RESEARCH, SR8-PLUS dissolution test station (HANSON RESEARCH, Chatsworth, Calif.) configured as a USP Apparatus 1, with the modification of 150 mL flasks. Approximately 0.5 g of each formulation (Examples 9–13) was placed in a separate mesh basket and then quenched in 50 mL portions of phosphate buffered saline (PBS, pH 7.4) receptor solution. The samples were maintained at 37° C. and continuously rotated at 100 rpm. Deionized water was added to the receptor solution daily to account for evaporation. Aliquots of 200 μL were removed every 1–2 days to analyze for protein content. Polypropylene collection vials were used to minimize protein adsorption.

The aliquots were analyzed using high performance liquid chromatography (HPLC) utilizing a reversed phase WATERS SYMMETRY C3 column (WATERS, Milford, Mass., Part No.: WAT200620) with a UV detection at 210 nm in a WATERS 2690-D separation module. Lysozyme concentrations were determined using a calibration curve of standards ranging from 5 to 550 μg/mL. Two determinations were made for each release experiment. Data for protein release over time are given in FIGS. 7 and 8.

Figure 7:
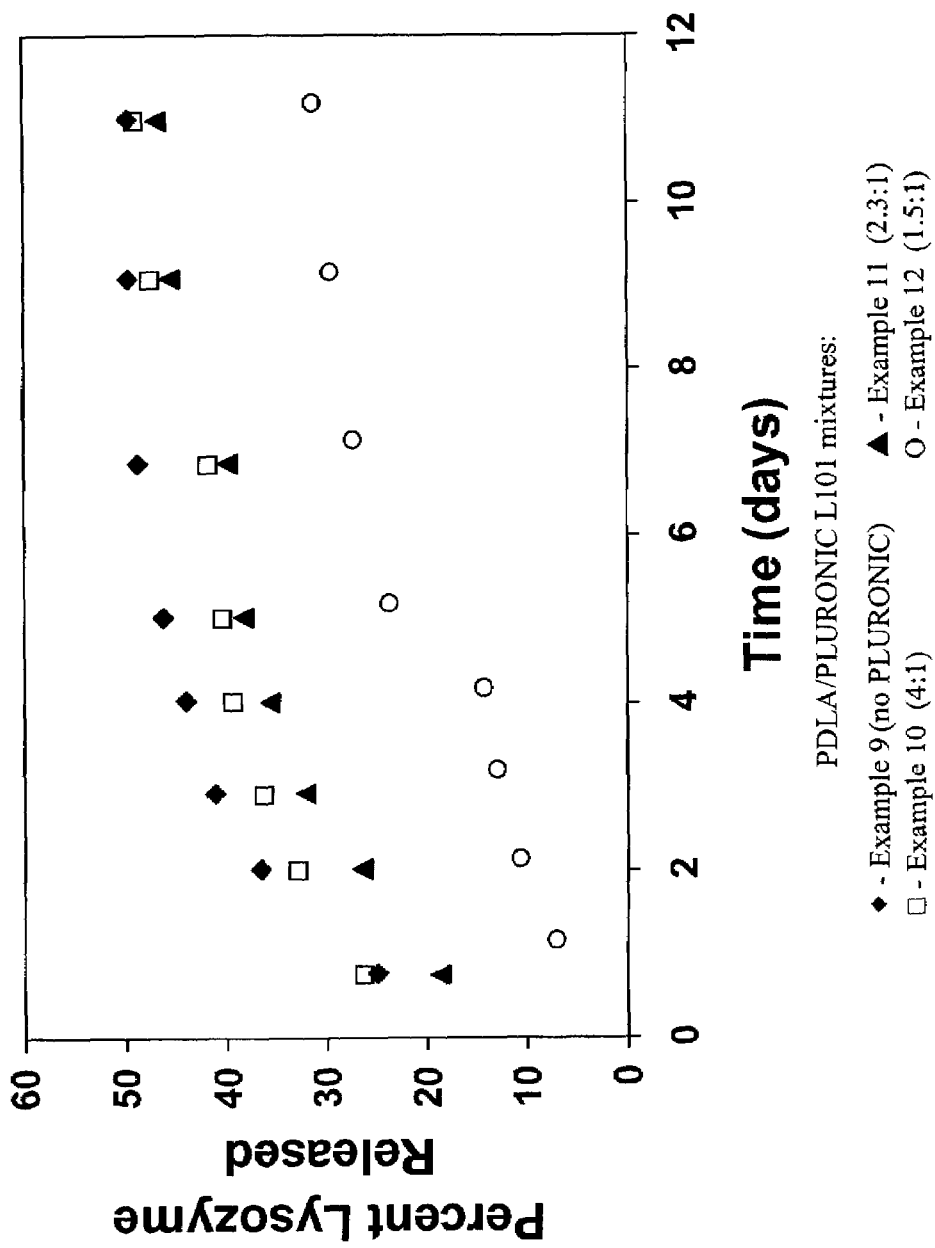
FIGS. 7–8 are graphs of results from protein release studies.

As shown in FIG. 7, increasing the amphiphilic block copolymer concentration in the mixture surprisingly leads to a decrease in the initial release rate (burst release) as well as a change in the overall release profile. The typical release curve for a PDLA/NMP system without amphiphilic block copolymer displays a profile characteristic of a rapidly precipitating system. This profile exhibits a large burst followed by a prolonged period of little protein release and eventual cessation of release (see P. D. Graham et al. *J. Control. Rel.* 58 (1999) 233–245; see also K. J. Brodbeck et al. *J. Control. Rel.* 62 (1999) 333–344). However, the depot with a 1.5:1 PDLA/L101 weight ratio exhibited minimal burst and an extended period of near constant rate protein release.

Figure 8:
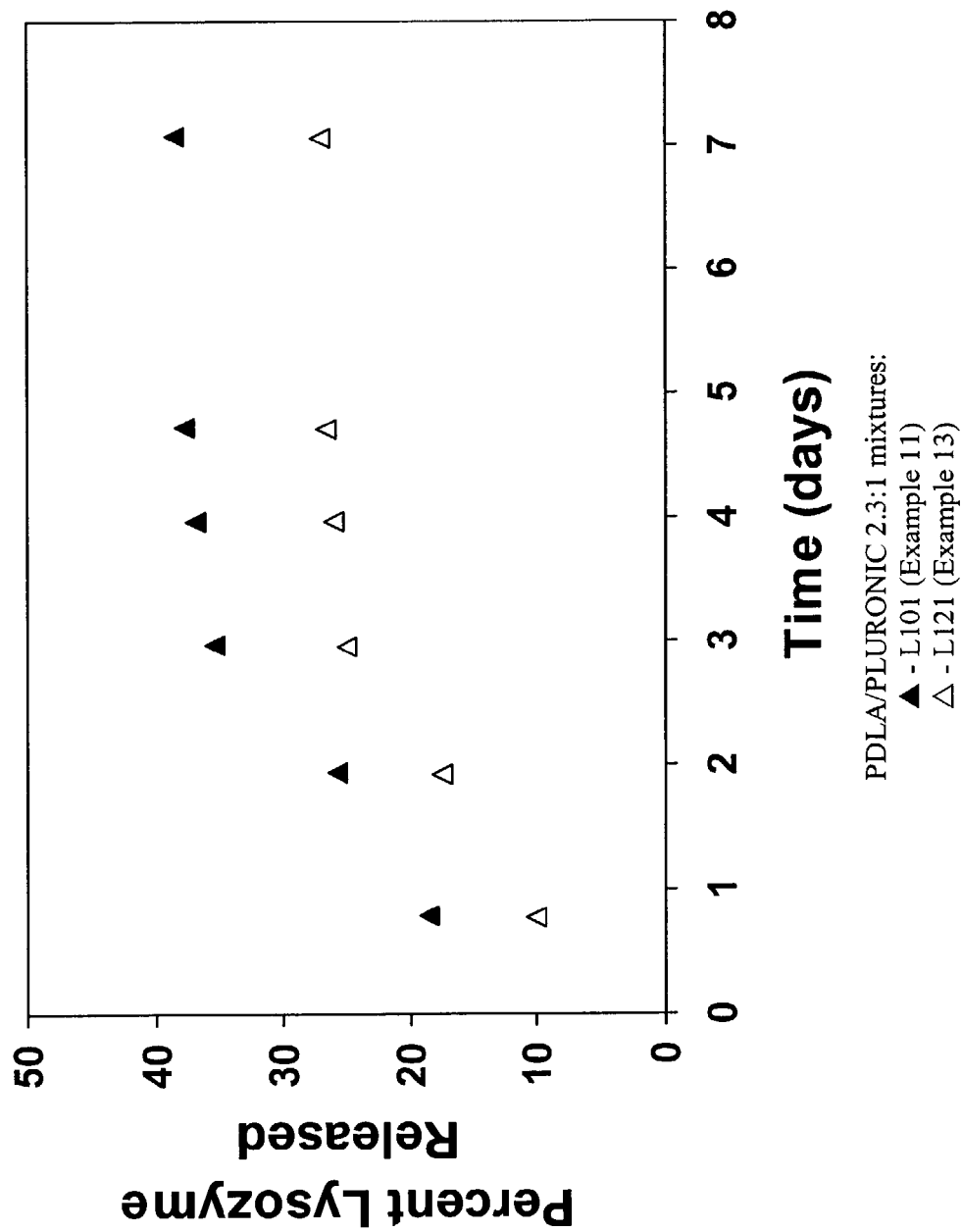

A surprising feature is that, although the magnitude of the protein burst systematically decreases with increasing amphiphilic block copolymer concentration, the corresponding phase separation rates increase (see FIG. 4). Thus, an increased concentration of amphiphilic block copolymer increased the speed of the phase separation of the depot, yet also decreased the degree of similarity of the release profile to that of conventional rapid phase separation systems (i.e. PDLA/NMP). FIG. 8 shows that the magnitude of the protein burst at a given amphiphilic block copolymer concentration decreases with increasing length of the hydrophilic poly(ethylene oxide) block (from L101 to L121). However, the shape of the release profile is similar for both block copolymers, suggesting that increasing the hydrophilic block length alone will not result in an extended release profile.

Example 15

Phase Behavior of Depots

Morphologies of the fully solidified depots from Examples 9–13 were examined using scanning electron microscopy (SEM). Samples were prepared by injecting approximately 0.5 g of polymer mixture into an aqueous bath at 37° C. The mixtures formed depots in the shape of disks of approximately 1.3 cm diameter and 0.3 cm thickness. The disks were removed from the bath after 15 days, fractured in liquid nitrogen, and dried under vacuum at room temperature for at least 24 hours. Samples for microscopy were sputter coated with an Au/Pd mixture using an EMSCOPE SC400 sputter coater. Micrographs were taken using a HITACHI S-530 SEM (HITACHI, LTD., Tokyo, Japan).

Phase segregation in samples of phase-separated depots was characterized using confocal microscopy. PLURONIC copolymers were labeled fluorescently with a tetramethylrhodamine-5-carbonyl azide dye (MOLECULAR PROBES) by reacting the polymer and dye in anhydrous dimethyl formamide (DMF) for 1 hour at 80° C. (A. Takadate et al. *Chem. Pharm. Bull.* 33 (1985) 1164–1169.) The modified PLURONIC copolymers were then used to make formulations as in Examples 3 and 4. Samples for microscopy were prepared by smearing the polymer mixture across an aluminum plate containing a 1.6 cm square depression with a depth of 380 μm, followed by immediate quenching in a room temperature water bath to induce coagulation for at least 24 h. The polymer films were fractured in liquid nitrogen and stored at −20° C. prior to analysis. Micrographs were taken using an OLYMPUS FLUOVIEW confocal microscope with a 543-nm helium neon laser, a 560-nm long-pass emission filter, and a 10× air objective lens.

No relationship was observed between the type and amount of PLURONIC block copolymer in the formulations and the morphologies imaged by SEM. Imaging by confocal microscopy, however, showed segregation of the amphiphilic block copolymer away from the polymer matrix. The amphiphilic block copolymer in the 2.3:1 PDLA/L101 depot (modified Example 3) preferentially segregated to the polymer-rich/polymer-lean interface during phase separation. Similar segregation effects were observed for all of the PLURONIC-containing systems, with the exception of the 1.5:1 PDLA/L101 depot (modified Example 4). In the 1.5:1 PDLA/L101 system, there appeared to be a significant amount of amphiphilic block copolymer located within the polymer-lean phase, as well as at the interface, implying that some amount of the block copolymer is leached out of the polymer-rich matrix.

The increased leaching of the amphiphilic block copolymer in the 1.5:1 PDLA/L101 system was also evident when PDLA/L101 depots were freeze-fractured in liquid nitrogen to expose the internal morphology, and then placed in small vials of water. The water containing the 1.5:1 PDLA/L101 depot became turbid, the water containing the 4:1 PDLA/L101 depot remained clear, and the 2.3:1 PDLA/L101 water had an intermediate level of turbidity. These observations suggest that, above a critical concentration enough amphiphilic block copolymer molecules leach into the polymer-lean phase to effectively fill the interconnected release pathway. Once in this phase, the block copolymer may form a sufficient diffusion barrier within the entire phase to prolong the protein release and to reduce or eliminate the premature burst.

Without wishing to be bound by any theory of interpretation it is believed that, as the poly(ethylene oxide) block length is increased, the hydrophilic segments may span a greater percentage of pores within the depot, resulting in a greater burst reduction in a PDLA/L121 system than in a comparable PDLA/L101 system. Regardless of the poly(ethylene oxide) chain length, however, it appears that a percentage of the pore size population is still sufficiently large that the protein is able to diffuse through the depot relatively unhindered by the presence of the poly(ethylene oxide) segments.

Obviously, numerous modifications and variations of the present invention are possible in light of the above teachings. It is therefore to be understood that within the scope of the appended claims, the invention may be practiced otherwise than as specifically described herein.

The invention claimed is:

1. A control led release injectable composition for delivery of a bioactive agent, comprising:
a non-aqueous biocompatible solvent;
a biodegradable hydrophobic polymer; and
an amphiphilic block copolymer comprising at least one segment of poly(ethylene oxide) and at least one segment of poly(propylene oxide);
wherein the biocompatible solvent is present in at least about 50 percent by weight of the composition the composition has a viscosity from about 0.1 Pa-s to about 10 Pa-s at 25° C., the amphiphilic block copolymer comprises a di-block copolymer, a tri-block copolymer, a multi-block copolymer or a graft copolymer,
a weight ratio of the biodegradable hydrophobic polymer to the amphiphilic block copolymer is from about 10:1 to about 1:1
the composition transforms into a depot upon contact with body fluid, and
when the composition is combined with a bioactive agent and administered to an organism, less than about 20% of the bioactive agent is released within 24 hours of administration and less than about 50% of the bioactive agent is released within 200 hours of administration.

2. The composition of claim 1, wherein the biocompatible solvent is miscible with water.

3. The composition of claim 1, wherein the biodegradable hydrophobic polymer comprises a polyester.

4. The composition of claim 1, wherein the amphiphilic block copolymer comprises a poly(ethylene oxide)-co-poly(propylene oxide)-co-poly(ethylene oxide) tri-biock copolymer.

5. The composition of claim 1, wherein the amphiphilic block copolymer comprises a poly(propylene oxide)-co-poly(ethylene oxide)-co-poly(propylene oxide) tri-block copolymer.

6. The composition of claim 1, wherein the weight ratio is from about 5:1 to about 1:1.

7. The composition of claim 1, wherein the biodegradable hydrophobic polymer has a weight average molecular weight from about 1,000 daltons to about 500,000 daltons; and
the amphiphilic block copolymer has a weight average molecular weight from about 500 daltons to about 250,000 daltons.

8. The composition of claim 1, wherein the biocompatible solvent is present in at least about 60 percent by weight of the composition.

9. The composition of claim 1, wherein the composition is sterile.

10. A controlled release injectable pharmaceutical composition, comprising:
a bioactive agent;
an amphiphilic block copolymer comprising at least one segment of poly(ethylene oxide) and at least one segment of poly(propylene oxide);
a biodegradable hydrophobic polymer; and
a non-aqueous biocompatible solvent;
wherein the biocompatible solvent is present in at least about 50 percent by weight of the composition the composition has a viscosity from about 0.1 Pa-s to about 10 Pa-s at 25° C., the amphiphilic block copolymer comprises a di-block copolymer, a tri-block copolymer, a multi-block copolymer or a graft copolymer,
a weight ratio of the biodegradable hydrophobic polymer to the amphiphilic block copolymer is from about 10:1 to about 1:1
the composition transforms into a depot upon contact with body fluid, and
when the composition is administered to an organism, less than about 20% of the bioactive agent is released within 24 hours of administration and less than about 50% of the bioactive agent is released within 200 hours of administration.

11. The composition of claim 10, wherein the biocompatible solvent is miscible with water.

12. The composition of claim 10, wherein the block copolymer is a poly(ethylene oxide)-co-poly(propylene oxide)-co-poly(ethylene oxide) tri-block copolymer.

13. The composition of claim 10, wherein the block copolymer is a poly(propylene oxide)-co-poly(ethylene oxide)-co-poly(propylene oxide) tri-block copolymer.

14. The composition of claim 10, wherein the weight ratio is from about 5:1 to about 1:1.

15. The composition of claim 10, wherein
the biodegradable hydrophobic polymer has a weight average molecular weight from about 1,000 daltons to about 500,000 daltons; and
the amphiphilic block copolymer has a weight average molecular weight from about 500 daltons to about 250,000 daltons.

16. The composition of claim 10, wherein the biocompatible solvent is present in at least about 60 percent by weight of the composition.

17. The composition of claim 15, wherein the composition is sterile.

18. A method of administering a bioactive agent, comprising: inserting the composition of claim 15 into an organism.

19. The method of claim 18, wherein the inserting is by injecting.

20. The method of claim 19, wherein the injecting comprises transmitting the composition through an 18-gauge or smaller needle.

21. The method of claim 19, wherein the injecting comprises transmitting the composition through a 20-gauge or smaller needle.

22. The method of claim 18, wherein less than about 10% of the bioactive agent is released within 24 hours of administration.

23. A method of making the composition of claim 1, comprising:
combining ingredients;
wherein the ingredients comprise the non-aqueous biocompatible solvent, the biodegradable hydrophobic polymer, and the amphiphilic block copolymer.

24. The method of claim 23, wherein the ingredients further comprise a bioactive agent.

25. The method of claim 23, wherein the amphiphilic block copolymer is a poly(ethylene oxide)-co-poly(propylene oxide)-co-poly(ethylene oxide) tri-block copolymer.

26. The method of claim 23, wherein the amphiphilic block copolymer is a poly(propylene oxide)co-poly(ethylene oxide)-co-poly(propylene oxide) tri-block copolymer.

27. The method of claim 23, wherein the biocompatible solvent is present in at least about 60 percent by weight of the composition.

28. A kit, comprising: a container; and the composition of claim 10.

29. The kit of claim 28, wherein the mixture comprises a unit dosage of the bioactive agent.

30. The kit of claim 28, further comprising a syringe.

31. The kit of claim 28, further comprising a septum.

32. The kit of claim 28, wherein the block copolymer comprises a poly(ethylene oxide)-co-poly(propylene oxide)-co-poly(ethylene oxide) tri-block copolymer.

33. The kit of claim 28, wherein the block copolymer comprises a poly(propylene oxide)-co-poly(ethylene oxide)-co-poly(propylene oxide) tri-block copolymer.

34. The kit of claim 28, wherein the weight ratio is from about 5:1 to about 1:1.

35. The kit of claim 28, wherein the biocompatible solvent is present in at least about 60 percent by weight of the composition.

36. The kit of claim 28, wherein the mixture is sterile.

37. The kit of claim 28, wherein the biocompatible solvent is miscible with water.

* * * * *

UNITED STATES PATENT AND TRADEMARK OFFICE
CERTIFICATE OF CORRECTION

PATENT NO. : 7,160,551 B2
APPLICATION NO. : 10/191789
DATED : January 9, 2007
INVENTOR(S) : Anthony J. McHugh and Jessica R. DesNoyer It is certified that error appears in the above-identified patent and that said Letters Patent is hereby corrected as shown below:

In the claims:

Col. 17, line 22, please delete "control led" and insert --controlled--.
Col. 17, line 30, please insert a comma after "composition".
Col. 17, line 30, please insert a return after "composition,".
Col. 17, line 32, please insert a return after "C.,".
Col. 17, line 38, please insert a comma after "1:1".
Col. 17, line 60, please insert a return after "wherein".
Col. 18, line 15, please insert a comma after "composition".
Col. 18, line 15, please insert a return after "composition,".
Col. 18, line 17, please insert a return after "C.,"
Col. 18, line 51, please delete "15" and insert --10--.
Col. 18, line 54, please insert a return after "prising:"
Col. 18, line 54, please delete "15" and insert --10--.
Col. 19, line 18, please insert a return after "comprising:".
Col. 19, line 18, please insert a return after "and"
Col. 19, line 21, please delete "bIoactive" and insert --bioactive--.

Signed and Sealed this

Twentieth Day of November, 2007

JON W. DUDAS
*Director of the United States Patent and Trademark Office*